United States Patent [19]

Edelman

[11] Patent Number: 4,681,104
[45] Date of Patent: Jul. 21, 1987

[54] APPARATUS FOR FOCUSING AN INTRAVASCULAR LASER CATHETER

[75] Inventor: William Edelman, Seal Beach, Calif.

[73] Assignee: Shiley Inc., Irvine, Calif.

[21] Appl. No.: 842,070

[22] Filed: Mar. 20, 1986

Related U.S. Application Data

[63] Continuation of Ser. No. 582,675, Feb. 23, 1984, abandoned.

[51] Int. Cl.⁴ ............................................. A61N 5/06
[52] U.S. Cl. .................................. 128/303.1; 128/398
[58] Field of Search ............... 128/6, 7, 303.1, 303.15, 128/395–398

[56] References Cited

U.S. PATENT DOCUMENTS

| | | | |
|---|---|---|---|
| 3,068,739 | 12/1962 | Hicks, Jr. et al. | 128/397 |
| 3,821,510 | 6/1974 | Muncheryan | 128/395 |
| 3,834,391 | 9/1974 | Block | 128/398 |
| 4,207,874 | 6/1980 | Choy | 128/6 |
| 4,211,229 | 7/1980 | Wurster | 128/395 |
| 4,217,891 | 8/1980 | Carson | 128/6 |
| 4,313,431 | 2/1982 | Frank | 128/303.1 |
| 4,392,485 | 7/1983 | Hiltebrandt | 128/6 |

Primary Examiner—William E. Kamm
Attorney, Agent, or Firm—P. C. Richardson; L. M. Donaldson; R. C. Turner

[57] ABSTRACT

An apparatus for directing laser energy to a vascular occlusion comprises a catheter and a plurality of optical fibers disposed in an annular array about a central axis at the outer wall of the catheter. The distal end of each fiber is beveled at an angle and is oriented away from the central axis and perpendicular to a plane formed by the central axis and the center of the distal end of the respective fiber, whereby the output of the fibers are directed toward the central axis and converge at a common focal point.

9 Claims, 5 Drawing Figures

APPARATUS FOR FOCUSING AN INTRAVASCULAR LASER CATHETER

BACKGROUND OF THE INVENTION

This is a continuation of application Ser. No. 582,675 filed on 2-23-84, now abandoned.

The present invention relates to a novel apparatus for directing laser energy to vascular obstructions. More particularly it relates to directing laser energy through an intravascular catheter to a fixed focal point in order to dissolve an occlusion in a blood vessel.

Current methods used to remove vascular obstructions such as fatty deposits, plague, calcification, and emboletic clots in occluded vessels include drug treatment using lysing agents, resection of the occluded vessel, displacement with embolectomy catheters, and balloon angioplasty. In using the embolectomy catheter, the clot must be located and isolated and then surrounded and removed. Balloon angioplasty increases the diameter of an occluded vessel by inflating a balloon and applying pressure stepwise to the sides of the occlusion. This technique is not useful when the vessel is completely occluded. There remains a need for an efficient device to destroy such lesions in situ without adverse side effects, even in completely occluded vessels.

U.S. Pat. No. 4,207,874 discloses a fiberoptic device with a coned head configuration at the distal end thereof. This configuration utilizes the coned head to bend the direction of the laser beam, thereby concentrating it near the distal end of the device.

SUMMARY OF THE INVENTION

The main object of the present invention is to direct laser energy to vascular obstructions in a controlled manner in order to dissolve and remove them. This object and others are achieved by the novel apparatus of the present invention which directs laser energy to an occlusion at a fixed focal point in a blood vessel, and is comprised of a catheter having proximal and distal ends and at least one lumen therethrough, and having a plurality of optical fibers having proximal ends adapted to receive a source of laser energy and having distal ends adapted to transmit the laser energy. The distal ends of the fibers are arranged into a parallel annular array about the outer wall of the catheter at the distal end of the catheter. Each fiber has the surface of the distal end beveled at a common angle, with the beveled surface being oriented away from the central axis and perpendicular to a plane formed by the central axis and the center of the distal end of the respective fiber. The laser energy is transmitted from each fiber toward the central axis to converge at a common point to focus the laser energy on the vascular obstruction.

The optical fibers may be, for example, fused silica, quartz or glass, and preferably the fiber bundle is enclosed in an outer annular sheath. In a preferred embodiment of the invention, the annular sheath is bifurcated in the vicinity of the proximal end forming a first leg which is adapted to receive the fibers, and a second leg enclosing the catheter. The first leg may be provided with means for association with an energy source, while the second leg terminates in an injection port provided with means for injecting contrast media or a therapeutic fluid through the lumen, or is provided with means for insertion of a guide wire through the lumen.

The present invention also embraces a method of reducing a vascular occlusion in situ comprising the steps of locating the position of the obstruction in situ, inserting the apparatus into the body of the patient, advancing it until the distal tip of the annular array of the solid optical fibers is spaced from the occlusion by the focal length of the apparatus, and firing the laser to reduce the obstruction.

As used herein, the term "to reduce a vascular obstruction", or the like, means to substantially reduce the size of the lesion. Preferably, of course, treatment is continued until essentially complete removal of the lesion has been achieved.

BRIEF DESCRIPTION OF THE DRAWINGS

Novel features and advantages of the present invention, in addition to those mentioned above, will become apparent from a reading of the following detailed description in conjunction with the accompanying drawings, wherein.

DESCRIPTION OF THE PREFERRED EMBODIMENT

Figure 1:
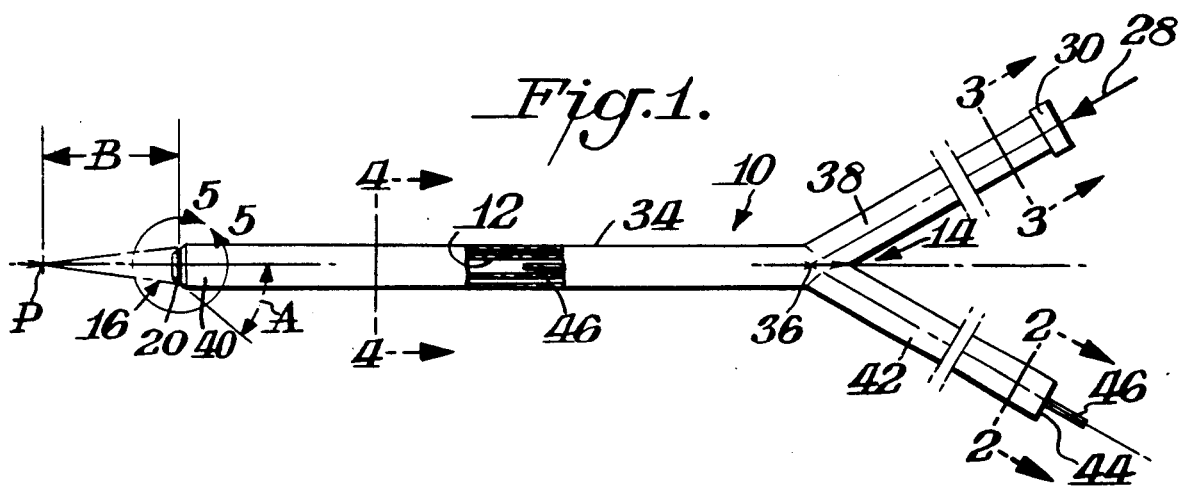
FIG. 1 is a side elevational view of a laser catheter of the present invention.
Figure 3:
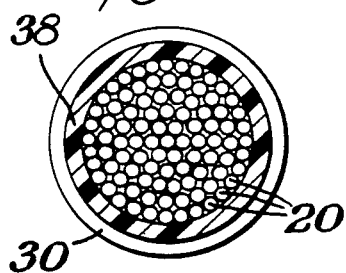
FIG. 3 is a cross-sectional view along the line 3—3 of FIG. 1.
Figure 2:
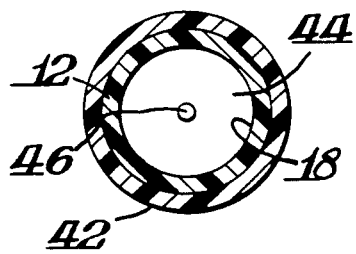
FIG. 2 is a cross-sectional view along the line 2—2 of FIG. 1.

In FIGS. 1-4 is depicted an apparatus 10 for directing laser energy to a fixed focal point in an occluded blood vessel, thereby dissolving and removing the occlusion. Apparatus 10 includes catheter 12 having proximal and distal ends 14, 16, respectively, and having a lumen 18 passing therethrough. A bundle of solid optical fibers 20, each having a core and a cladding of different refractive indices, is arranged in an annular array around the outer wall 22 of the catheter 12. Fibers 20 are adapted at their proximal end for association with a laser energy source 28 through a coupling 30. The optical fibers 20 may be glass or quartz, but are preferably fused silica.

The diameter of the optical fibers 20 is generally between about 0.001 inches and 0.050 inches, preferably 0.001 inches to 0.020 inches. The length of the fibers 20 is generally about 50 to 300 cm., preferably 100 to 150 cm. The number of fibers in the bundle, which is arranged in annular array around the outer wall 22, is typically between about 35 and 100, preferably 50 to 75.

In a preferred embodiment, apparatus 10 is provided with an outer annular sheath 34, preferably made from a flexible material, especially silicone rubber tubing, enclosing fiber bundle 20. Sheath 34 is bifurcated at 36 in the vicinity of the proximal end thereof, forming a first leg 38 through which are fed fibers 20 which transmit laser energy from source 28 to distal end 40 of the fiber bundle. Sheath 34 at bifurcation 36 also extends to second leg 42 enclosing catheter 12. Second leg 42 of sheath 34 terminates in an injection port 44 for insertion of guide wire 46 through lumen 18. The guide wire is typically radiopaque. Alternatively, injection port 44 may be provided with reservoir containing contrast medium or therapeutic fluid for injection through lumen 18. The therapeutic fluid may be, for example, saline to rinse the vessel, thrombogentic agents to dissolve clots, or vasodilators or enlarge the vessel.

Figure 4:
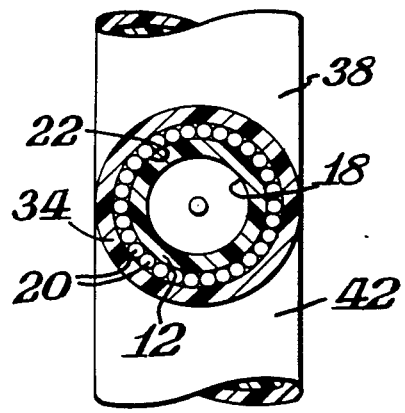
FIG. 4 is a cross-sectional view along the line 4—4 of FIG. 1.
Figure 5:
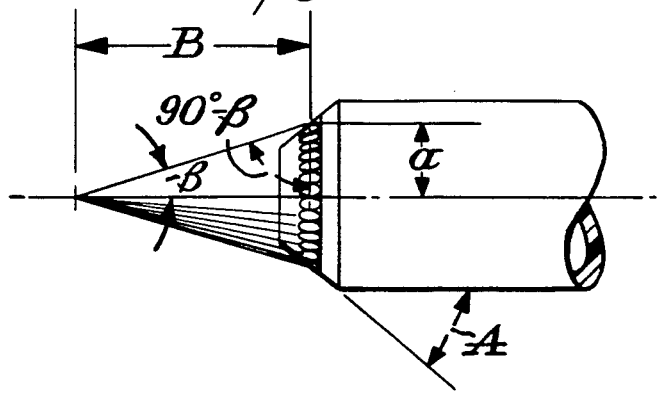
FIG. 5 is an enlarged view of a portion of the catheter delineated by 5—5 of FIG. 1.

In accordance with the present invention, as shown particularly in FIGS. 4 and 5, the bundle of fibers 20 are arranged into an annular array at the distal end 16 of the catheter 12. The surfaces of the distal ends 40 of the fibers are beveled at an angle A. It is known that the laser energy will be transmitted from the beveled surface at an angle $\beta$, where:

$$\beta = \sin^{-1}\left[\left(\frac{N_1}{N_2}\right)\sin A\right] - A \quad (1)$$

By orienting the beveled surface away from the central axis and perpendicular to a plane formed by the central axis and the center of the distal end of the fiber, the laser energy will be transmitted at the angle $\beta$ and through the central axis of the catheter. By orienting each of the respective fibers in this manner, the laser energy will be transmitted from each fiber through the central axis and generally converge at a common focal point P.

The focal distance B can be further defined (see FIG. 5) in terms of the radius, a, of the array as follows:

$$\frac{\sin(90° - \beta)}{B} = \frac{\sin \beta}{a} \quad (2)$$

$$\text{therefore } B = \frac{[\sin(90° - \beta)]a}{\sin \beta}$$

and substituting equation (1) for $\beta$ into equation (2) yields $$B = \left[\frac{\sin\left(90° - \sin^{-1}\left[\left(\frac{N_1}{N_2}\right)\sin A\right] - A\right)}{\sin\left[\sin^{-1}\left(\left(\frac{N_1}{N_2}\right)\sin A\right] - A\right)}\right]a \quad (3)$$

where:
$N_2$ = index of refraction of the optical fiber clad
$N_1$ = index of refraction of the optical fiber core
a = radius of the annular array of fibers from catheter axis to center of fiber core
A = bevel angle
B = focal length The catheter diameter and materials of construction of the optical fibers are factors in the relationship between the bevel angle and focal length. Thus, for example, when $N_2$ is 1.402, $N_1$ is 1.492 (as for a typical quartz fiber) and a is 0.035 inches, the focal length depends on the bevel angle as shown in the following table:

| (°) a | B (in) |
|---|---|
| 0 | Infinity |
| 10 | 3.115 |
| 30 | 0.945 |
| 50 | 0.420 |
| 70 | 0.105 |

Accordingly, when a, $N_1$ and $N_2$ are given, a desired focal length can be obtained by appropriate selection of the corresponding bevel angle. For the reduction of vascular obstructions, a focal length of from about 0.100 in. to about 0.200 in. is preferred.

In use, the occlusion is located by angiography, or percutaneous puncture. The laser catheter is then advanced through an arteriotomy up to the occlusion. In peripheral arteries contrast media is injected through the catheter to locate the occlusion with a fluoroscope. With the distal tip of the annular array of fibers spaced from the occlusion by the fixed focal length of the device, the laser is then fired to destroy the occlusion. With coronary arteries the contrast media is injected through the catheter to locate the coronary arterial tree. A guide wire is threaded through the catheter into the selected arterial segment, until it comes into contact with the occlusion, the radiopaque nature of the guide wire facilitating the detection of position of the occlusion by fluoroscopy.

The catheter is then threaded over the guide wire to a position proximal to the distal tip of the guide wire, which is substantially equal to the focal length B of the catheter as determined by the beveled angle A.

The fixed focal point laser catheter of the present invention eliminates many of the problems of previously used methods for removal of vascular obstructions, and provides a disposable, relatively simple system, which substantially focuses the laser energy at a single fixed, preset point, thereby eliminating the risk of accidental perforation of the vessel. The novel device of this invention has the further advantage of being effective even in a completely occluded vessel. In addition, it is of relatively uncomplicated design, offers easy manipulation and insertion, and is adapted for use with known laser energy sources.

Further modifications will occur to those skilled in the art. The scope of the invention is defined by the appended claims and should not be understood as limited by the specific embodiments described herein.

I claim:
1. Apparatus for directing laser energy comprising:
a plurality of optical fibers having proximal ends adapted to receive a source of laser energy and having distal ends which transmit the laser energy;
said apparatus having a central axis and having a point on the central axis;
said distal ends of the fibers arranged into a parallel annular array about the point on the central axis;
said fibers having a surface beveled at a common angle on the distal ends thereof; and
said beveled surfaces being oriented away from the central axis and perpendicular to a plane formed by the central axis and the center of the distal end of the respective fiber, whereby the laser energy associated with the apparatus is transmitted from each fiber toward the central axis to converge substantially at a common focal point.

2. The apparatus of claim 1 wherein the radius of the annular array of said distal ends of said fibers is about 0.035 inches, and said beveled surfaces of said fibers are beveled at about 70°, whereby the laser energy associated with the apparatus is transmitted from said fibers to substantially converge on the central axis at about 0.100 inches forward of said distal ends of said fibers.

3. The apparatus of claim 1 further comprising a source of laser energy coupled to said proximal end of said fibers.

4. The apparatus of claim 3 further comprising a source of laser energy coupled to said proximal ends of said fibers.

5. Apparatus for focusing the laser energy associated with an intravascular laser catheter comprising:

a catheter having a central axis, proximal and distal ends, an outer wall, and at least one lumen therethrough;

a plurality of optical fibers having proximal ends adapted to receive a source of laser energy and having distal ends which transmit the laser energy;

said distal ends of said fibers arranged into a parallel annular array about the central axis at the outer wall of said catheter and at the distal end of said catheter;

said fibers having a surface beveled at a common angle, on the distal ends thereof; and said beveled surfaces being oriented away from the central axis and perpendicular to a plane formed by the central axis and the center of the distal end of the respective fiber, whereby the laser energy associated with the apparatus is transmitted from each said fiber toward the central axis to converge substantially at a common focal point.

6. The apparatus of claim 5 further comprising a guide wire inserted through the lumen of said catheter to facilitate the positioning of said catheter within an arteriotomy of a human patient adjacent to an occlusion, whereas said guidewire is removeable after the catheter is positioned.

7. The apparatus of claim 5 further comprising an outer annular sheath enclosing said fibers.

8. The apparatus of claim 7 wherein said sheath is bifurcated in the vicinity of the proximal end thereof, whereby a first leg receives and encloses said fibers, and a second leg interconnects with said lumen and is adapted to receive a guide wire to facilitate positioning of said catheter within an arteriotomy of a human patient adjacent to an occlusion.

9. The apparatus of claim 8 wherein the radius of the annular array of said distal ends of the fibers is about 0.035 inches, and the surfaces of said fibers are beveled at about 70°, whereby the laser energy associated with the apparatus is transmitted from each said fiber to substantially converge on the central axis at about 0.100 inches forward of said distal ends of said fibers.

* * * * *